United States Patent
Berry, III

[11] Patent Number: 6,138,850
[45] Date of Patent: Oct. 31, 2000

[54] MODULAR STERILIZATION CONTAINER

[75] Inventor: Bernie B. Berry, III, Indianapolis, Ind.

[73] Assignee: Carr Metal Products, Inc., Indianapolis, Ind.

[21] Appl. No.: 09/020,889

[22] Filed: Feb. 9, 1998

[51] Int. Cl.[7] .................................................. B65D 6/24
[52] U.S. Cl. ..................... 220/4.28; 220/770; 220/771; 220/768; 206/370; 206/369
[58] Field of Search .................. 206/370, 369; 220/326, 4.33, 4.28, 770, 771, 768, 772, 212.5, 324

[56] References Cited

U.S. PATENT DOCUMENTS

| | | | |
|---|---|---|---|
| 3,854,582 | 12/1974 | Martinelli | 206/508 |
| 3,987,924 | 10/1976 | Uitz | 220/4.28 |
| 4,643,303 | 2/1987 | Arp et al. . | |
| 4,798,292 | 1/1989 | Hauze . | |
| 5,084,251 | 1/1992 | Thomas . | |
| 5,215,726 | 6/1993 | Kudla et al. . | |
| 5,284,632 | 2/1994 | Kudla et al. . | |
| 5,310,049 | 5/1994 | Bigelow et al. | 206/53 |
| 5,346,677 | 9/1994 | Risk . | |
| 5,424,048 | 6/1995 | Riley . | |
| 5,433,929 | 7/1995 | Rihimaki et al. . | |
| 5,451,379 | 9/1995 | Bowlin, Jr. . | |
| 5,474,196 | 12/1995 | Fausel et al. | 220/4.28 |
| 5,518,115 | 5/1996 | Latulippe . | |
| 5,524,755 | 6/1996 | Deeds . | |
| 5,540,901 | 7/1996 | Riley . | |
| 5,560,508 | 10/1996 | Hsu | 220/4.31 |
| 5,593,058 | 1/1997 | Spencer et al. | 220/4.31 |
| 5,678,717 | 10/1997 | Hsu | 220/4.28 |
| 5,843,387 | 12/1998 | Dane et al. | 422/300 |
| 5,913,422 | 6/1999 | Cote et al. | 206/370 |
| 5,918,740 | 7/1999 | Berry, Jr. | 206/369 |

*Primary Examiner*—Stephen Castellano
*Attorney, Agent, or Firm*—Woodard, Emhardt, Naughton, Moriarty & McNett

[57] ABSTRACT

A container for sterilization of medical devices. A container of modular construction is described comprising separable sides, separable corner pieces, and a separable bottom panel. Two opposing sides are of a modular length, and thus by substituting sides of a different length the interior volume of the container may be changed. The container also includes a removeable lid with latching mechanisms on opposing ends. The lid and latching mechanisms are generally flush with the exterior surface of the container.

23 Claims, 8 Drawing Sheets

MODULAR STERILIZATION CONTAINER

BACKGROUND OF THE INVENTION

The present invention relates generally to containers useful for sterilization of medical devices. However, certain applications of the present invention may be outside of this field.

The use of a container for the sterilization and storage of medical devices is well known. The container is provided with a particular selection of devices for a particular medical procedure. The devices are placed within a container and the container is then subjected to the heat and sterilant (water and/or chemicals) necessary to sterilize the devices. Subsequent to sterilization, the container may be wrapped within a sterile covering and stored until required.

Various designs have been offered for sterilization containers. Some of these designs can be found in the following U.S. patents:

| Patent No. | Inventor | Issue Date |
|---|---|---|
| 4,798,292 | Hauze | Jan. 17, 1989 |
| 4,643,303 | Arp et al. | Feb. 17, 1987 |
| 5,284,632 | Kudla et al. | Feb. 8, 1994 |
| 5,215,726 | Kudla et al. | Jun. 1, 1993 |
| 5,451,379 | Bowlin, Jr. | Sep. 19, 1995 |
| 5,524,755 | Deeds | Jun. 11, 1996 |
| 5,084,251 | Thomas | Jan. 28, 1992 |
| 5,433,929 | Riihimaki et al. | Jul. 18, 1995 |
| 5,346,677 | Risk | Sep. 13, 1994 |
| 5,518,115 | Latulippe | May 21, 1996 |
| 5,540,901 | Riley | Jul. 30, 1996 |
| 5,424,048 | Riley | Jun. 13, 1995 |

These designs generally depict containers comprising a lower tray and an upper tray or lid. The lower and upper trays are generally of a fixed, unitary construction. The lower tray and the upper tray or lid are generally of a particular size and shape which cannot be altered without damaging or destroying the trays. Some of these designs have an internal volume satisfactory for the quantity of devices necessary for a particular medical procedure, but insufficient volume for a larger number of devices required by a different medical procedure. Likewise, the containers resulting from some of these designs may be too large for a particular medical procedure, and thus be inefficient in terms of space and cost.

There is a continuing need for improvements in the field of sterilization containers and the present invention provides a novel and unobvious apparatus for an improved sterilization container.

SUMMARY OF THE INVENTION

One embodiment of the present invention provides a container for sterilizaton of medical devices. The container includes a plurality of separable sides and a plurality of separable corner pieces. Each side is coupled to at least one of the corner pieces. The container also includes a separable bottom coupled to at least one of the sides or corner pieces.

It is an object of the present invention to provide an improved container for sterilization of medical devices.

These and other objects and advantages of the present invention will be apparent from the description of the preferred embodiment, the drawings, and the claims that follow.

BRIEF DESCRIPTION OF THE DRAWINGS

FIG. 6 is a right side perspective view of the apparatus of FIG. 4 with a portion of the apparatus pushed in.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1A:
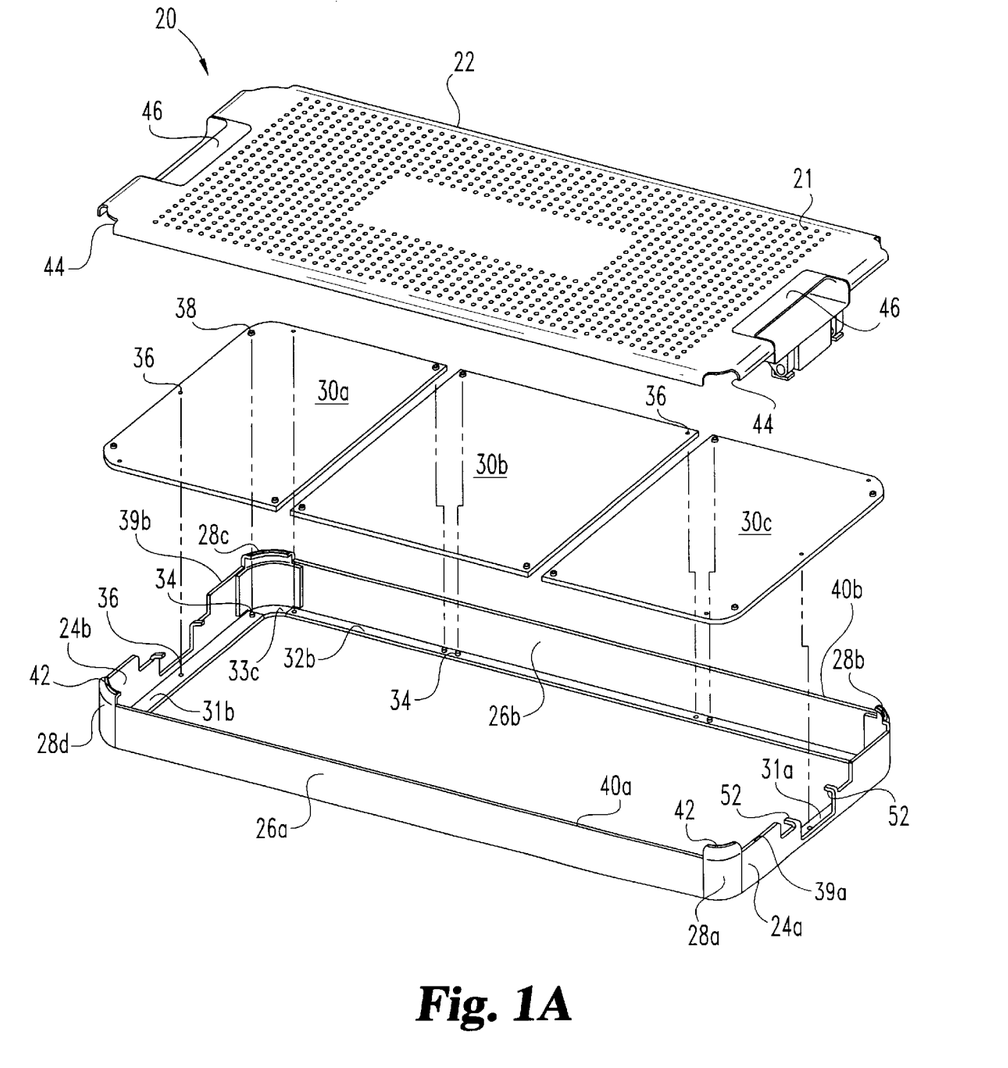
FIG. 1A is a top, front, and right side exploded perspective view of an apparatus according to one embodiment of the present invention.

FIG. 1A is a top, front, and right side exploded perspective view of a sterilization container 20 useful for sterilization of medical instruments and devices according to one embodiment of the present invention. Container 20 includes a removeable lid 22, opposing separable sides 24a and 24b, opposing separable sides 26a and 26b, corner pieces 28a, 28b, 28c, and 28d, and bottom pieces 30a, 30b, and 30c. Removeable lid 22 includes a plurality of passage holes 21 defined therein for passage of sterilant fluid into and out of the interior of container 20. Lid 22 is releaseably coupled to opposing separable sides 24a and 24b by a latching mechanism to be described later (see FIGS. 3–9). Separable side 24a is coupled at one end to corner piece 28a and at the other end to corner piece 28b. Separable side 24b is coupled at one end to corner piece 28c and at the other end to corner piece 28d. Separable side 26a is coupled to corner pieces 28a and 28d, and separable side 26b is coupled to corner pieces 28b and 28c. Separable sides 26a and 26b are of a predetermined, modular length.

A bottom panel 30 comprising bottom pieces 30a, 30b, and 30c is in contact with and preferably supported by substantially flat ledges that extend in a generally perpendicular manner from the vertical walls of separable sides 24a, 24b, 26a, and 26b. Separable sides 24a and 24b include ledges 31a and 31b, respectively, for supporting bottom pieces 30c and 30a, respectively. Separable sides 26a and 26b include ledges 32a and 32b, respectively, for supporting bottom pieces 30a, 30b, and 30c. Additional support of bottom panel 30 is preferably provided by substantially flat ledges that extend from the corner pieces. Ledges 33a and 33b of corner pieces 28a and 28b, respectively, support bottom piece 30c. Ledges 33c and 33d of corner pieces 28c and 28d, respectively, support bottom piece 30a. In some embodiments of the present invention bottom panel 30 defines a plurality of attachment holes (not shown) to which fixtures may be attached which are useful for clamping medical devices thereto.

Ledges 31a, 31b, 32a, and 32b incorporate a combination of pins 34 and fastener holes 36 that align with locating holes 38 and fastener holes 36, respectively, on bottom panel 30. Fasteners (not shown) fasten bottom piece 30a to ledges 32a, 32b, and 31b. Bottom piece 30c is similarly fastened to ledges 32a, 32b, and 31a. Bottom piece 30b is fastened to ledges 32a and 32b. Pins 34 protrude through locating holes 38 and generally align bottom panel 30 relative to sides 24a, 24b, 26a, and 26b. Bottom panel 30 preferably includes a short cylinder protruding above the upper surface of bottom panel 30 and around hole 38 so as to provide additional bearing area for pin 34. However, the present invention also contemplates a locating hole 38 defined only within bottom panel 30. Also, although it is preferable to include pins 34 and fastener holes 36 within ledges 31a, 31b, 32a, and 32b, the present invention also contemplates pins 34 or fastener holes 36 as part of ledges 33a, 33b, 33c, and 33d of corner pieces 28a, 28b, 28c, and 28d, respectively. Bottom pieces 30a, 30b, and 30c are repeatedly separable from sides 24a, 24b, 26a, and 26b, and/or from corners 28a, 28b, 28c, and 28d, by removal of the fasteners through holes 36.

Figure 1B:
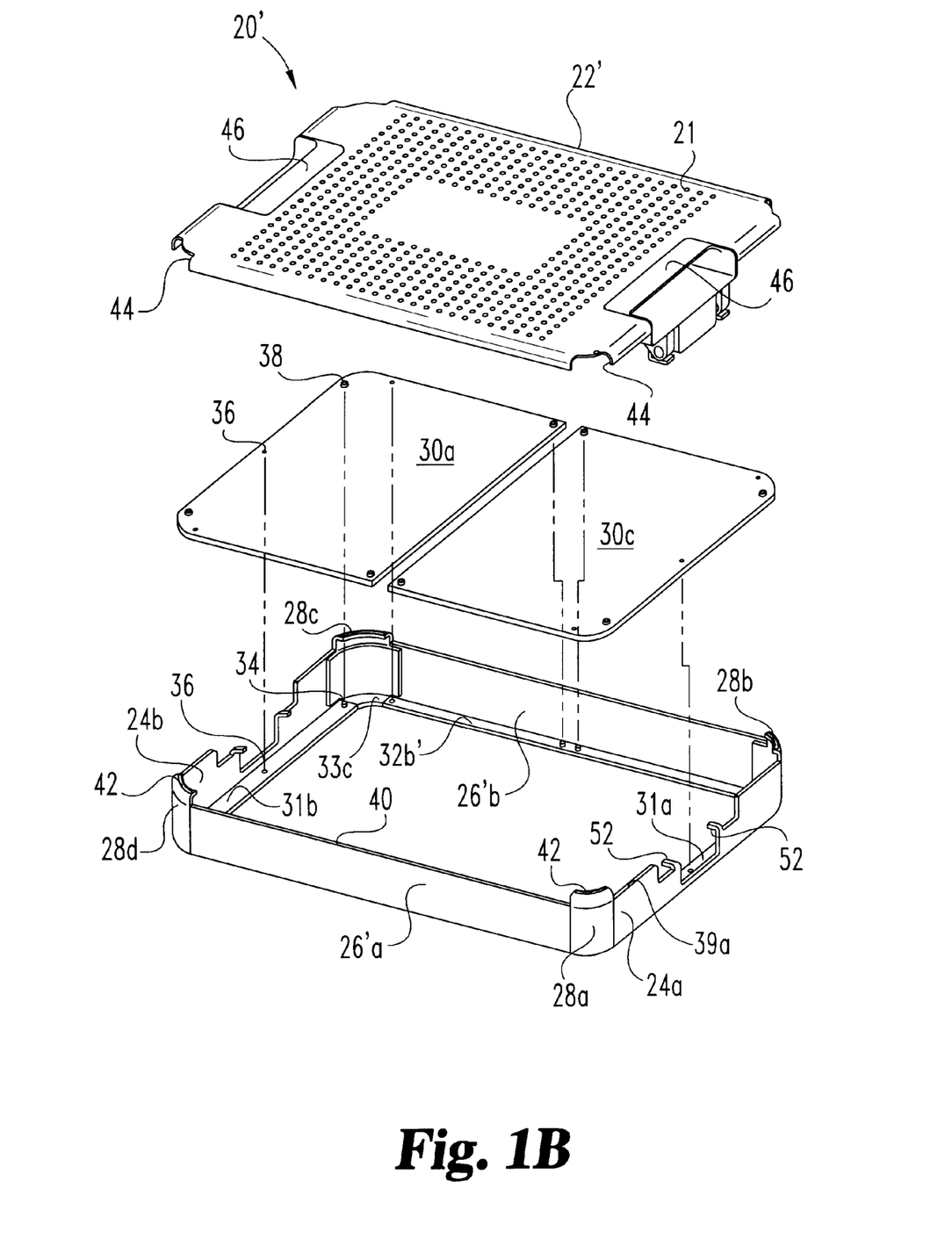
FIG. 1B is a top, front, and right side exploded perspective view of an apparatus according to another embodiment of the present invention.

FIG. 1A shows one embodiment of the present invention in which three bottom pieces 30a, 30b, and 30c provide a bottom panel 30 of a predetermined length useful with the predetermined lengths of opposing sides 26a and 26b. However, the present invention contemplates modularity of the length of container 20, and thus modularity of the internal volume of container 20. A container 20 is shown in FIG. 1B. Container 20' incorporates a lid 22' of a shorter length than lid 22. Container 20' also includes opposing sides 26a' and 26b' of a shorter length than opposing sides 26a and 26b. Bottom panel 30' comprises bottom pieces 30a and 30c, with bottom piece 30b being omitted. Thus, container 20 with a first, larger internal volume may be converted into a container 20' with a second, smaller internal volume by substitution of separable side 26a' for 26a, substitution of separable side 26b' for separable side 26b, omission of bottom piece 30b, and substitution of lid 22'. Container 20 may also be converted into a container (not shown) with an internal volume larger than the internal volume of container 20. One improvement offered by the present invention is that a healthcare provider such as a hospital can reduce its equipment cost by rebuilding sterilization containers made in accordance with the present invention into different sizes, both larger and smaller than apparatus 20, and thus avoid the cost of purchasing new containers.

Although apparatus 20 and 20' have been described having multi-piece bottom panels 30 and 30', respectively, the present invention also contemplates a single piece bottom panel 30 and a single piece bottom panel 30' of different lengths. Further, although apparatus 20 and 20' have been described incorporating a plurality of corner pieces separable from the sides of the container, the present invention also contemplates those embodiments in which corner pieces are integral with sides otherwise similar to sides 24a and 24b, In these embodiments the corner pieces are not separable from the sides, but modularity of the present invention is maintained by the separability of opposing sides 26a and 26b.

Corner pieces 28a–d include a first alignment feature 42 that is preferably spaced above the upper surfaces of adjacent separable sides. Lid 22 includes a second alignment feature 44 which is generally complementary in shape to first alignment feature 42. Coupling of lid 22 to sides 24a and 24b results in coupling of first alignment feature 42 with second alignment feature 44. Separable sides 24a and 24b incorporate upper surfaces 39a and 39b, respectively, and separable sides 26a and 26b incorporate upper surfaces 40a and 40b, respectively. Although one embodiment of the present invention includes a first alignment feature 42 spaced above the upper surfaces of the separable sides, the present invention also contemplates those embodiments in which first alignment feature 42 is recessed below upper surfaces 39a and 39b, and 40a and 40b, and second alignment feature 44 includes a protrusion to fit within the recess. Also, although upper surfaces 39a, 39b, 40a, and 40b are generally at the same elevation above bottom panel 30, the present invention also contemplates upper surfaces 39a, 39b, 40a, and 40b that are at different elevations.

Lid 22 Includes a pair of handles 46 on opposing ends of lid 22 as best seen in FIGS. 1A, 1B, and a. Handle 46 includes within it a pocket 48 for carrying container 20 Pocket 48 has a shape suitable for insertion of human fingers. Lid 22 also includes a button 50 coupled to lid 22 and moveable relative to lid 22. Handle 46 is attached to lid 22 by a pair of ears 54 best seen in FIG. 3 and FIG. 4. A pair of flush mounted fasteners 56 attach handle 46 to lid 22 through ears 54.

Figure 2:
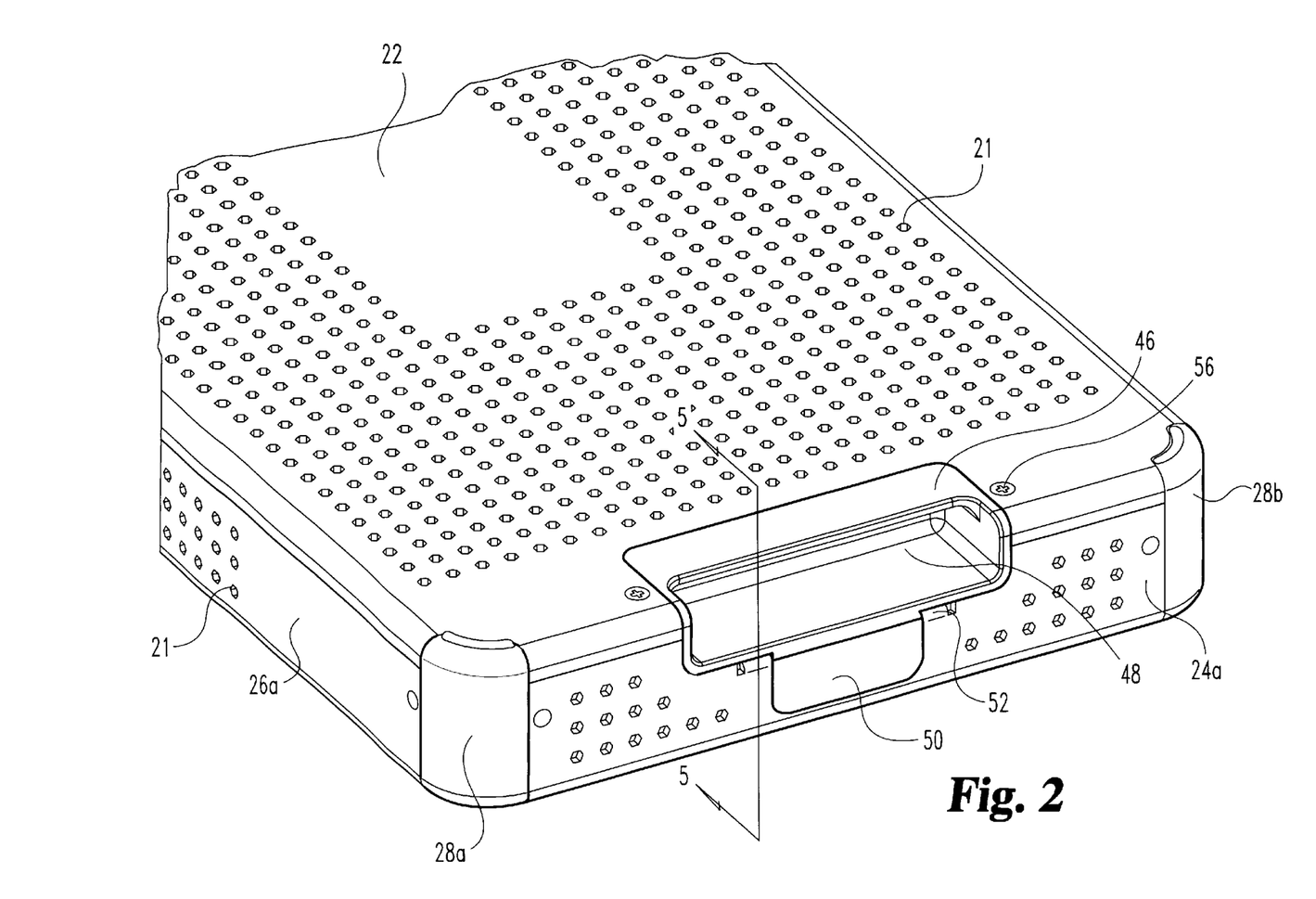
FIG. 2 is a partial perspective view of a portion of the apparatus of FIG. 1A.
Figure 3:
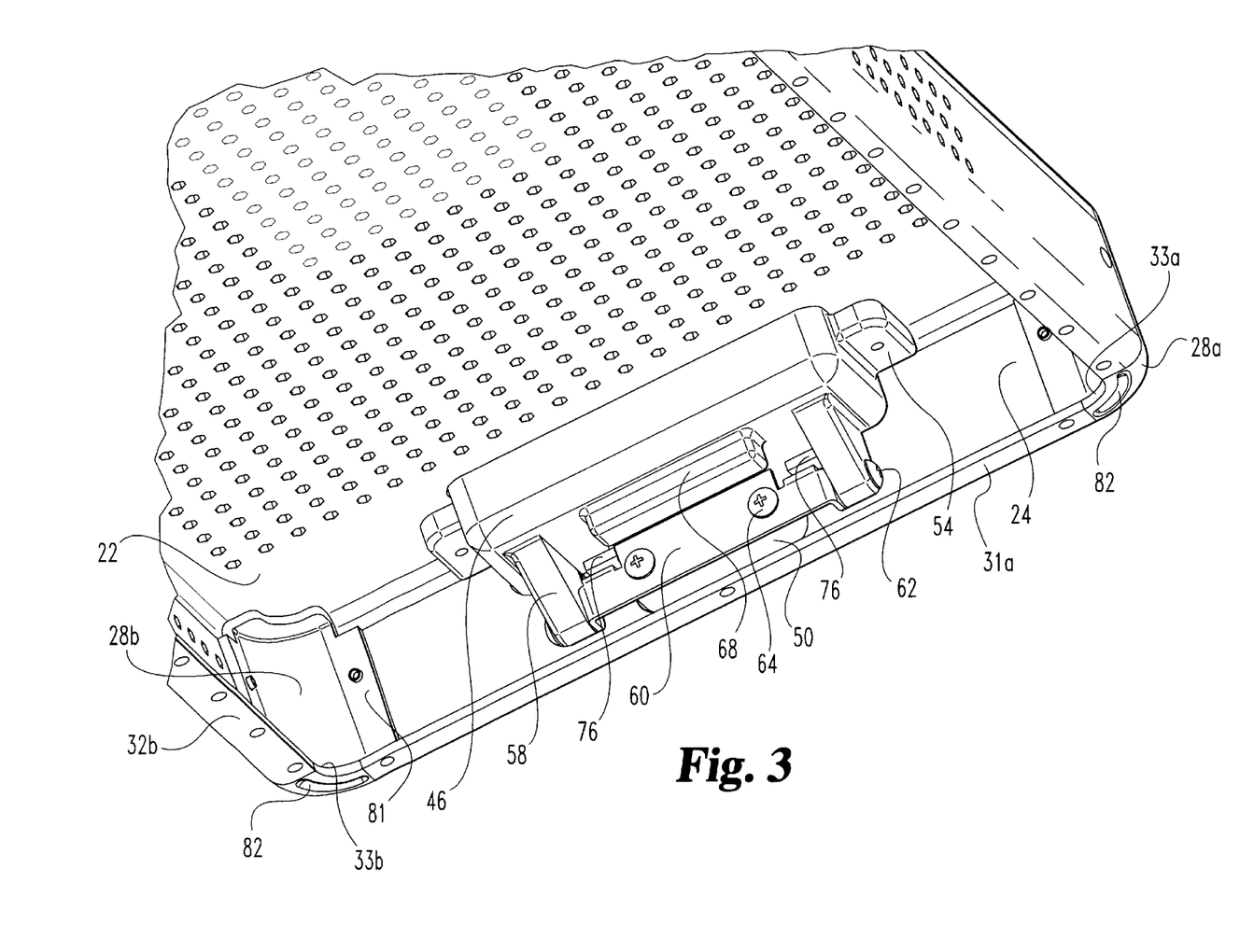
FIG. 3 is a partial perspective view of a portion of the apparatus of FIG. 1A with a bottom piece removed.
Figure 4:
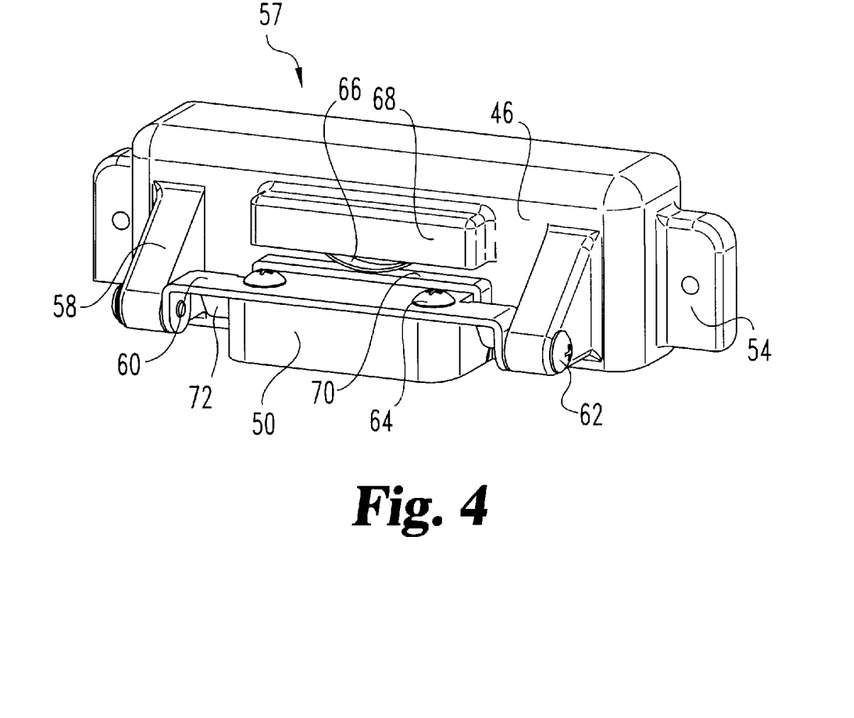
FIG. 4 is a bottom perspective view of a handle assembly comprising a portion of the present invention.

Handle 46 and button 50 are substantially flush with the exterior surface of container 20. The exterior surface of container 20 is also generally smooth. By being generally smooth and not having abrupt protrusions beyond its exterior surfaces, container 20 is especially suitable for being wrapped in a protective covering after sterilization with little danger of the protective covering being ripped, abraded, broken, or damaged by the exterior surface of container 20. FIGS. 2 and 3 also show a plurality of holes 21 for passage of sterilant defined within sides 24 and 26. In some embodiments of the present invention a plurality of holes 21 for passage of sterilant are defined within bottom panel 30.

Sides 24a and 24b each include a pair of stationary tabs 52 which are generally flush with the exterior surface of sides 24a and 24b, and which project inwardly toward the interior of container 20, as best seen in FIG. 1. Stationary tabs 52, along with other elements of the latching mechanism of container 20, provides a means for releaseably coupling lid 22 to sides 24a and 24b. The latching mechanism of apparatus 20 is best understood by referring to FIGS. 3, 4, 5, and 6. Extending generally downward from the underside of handle 46 are a pair of supports 58. A latchplate 60 is pivotally connected to supports 58 by a pair of pivoting fasteners 62 operating through pivot hole 63a of support 58 and hole 63b of latchplate 60 (see FIG. 7 and 9). Button 50 is coupled to latchplate 60 by a pair of fasteners 64, and is moveable with latchplate 60. A spring 66 located within a spring retainer 68 presses against back surface 70 of button 50 and thus urges button 50 and latchplate 60 to pivot in a direction whereby upper exterior surface 71 of button 50 is urged outward.

Figure 5:
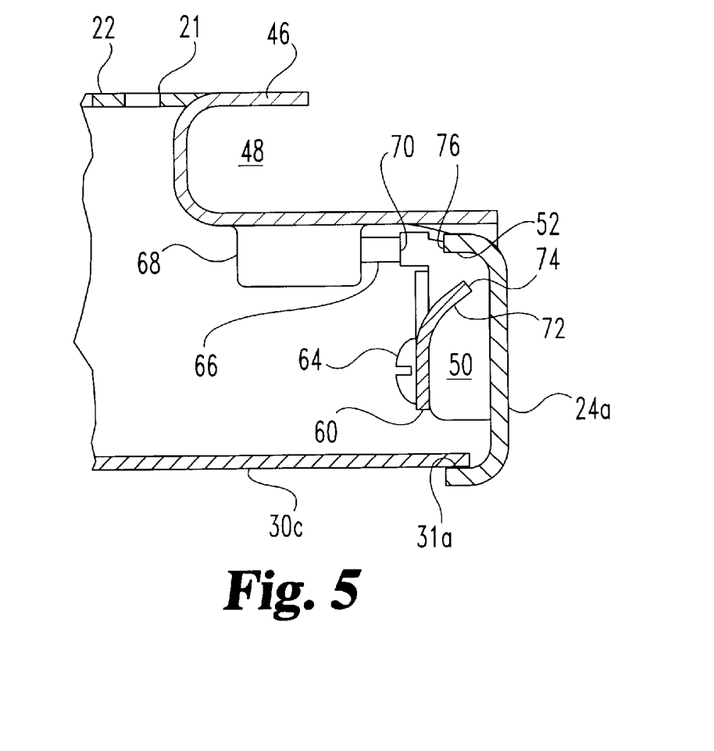
FIG. 5 is a partial front elevational view in full section of the apparatus of FIG. 2 as taken along line 5—5 of FIG. 2.
Figure 6:
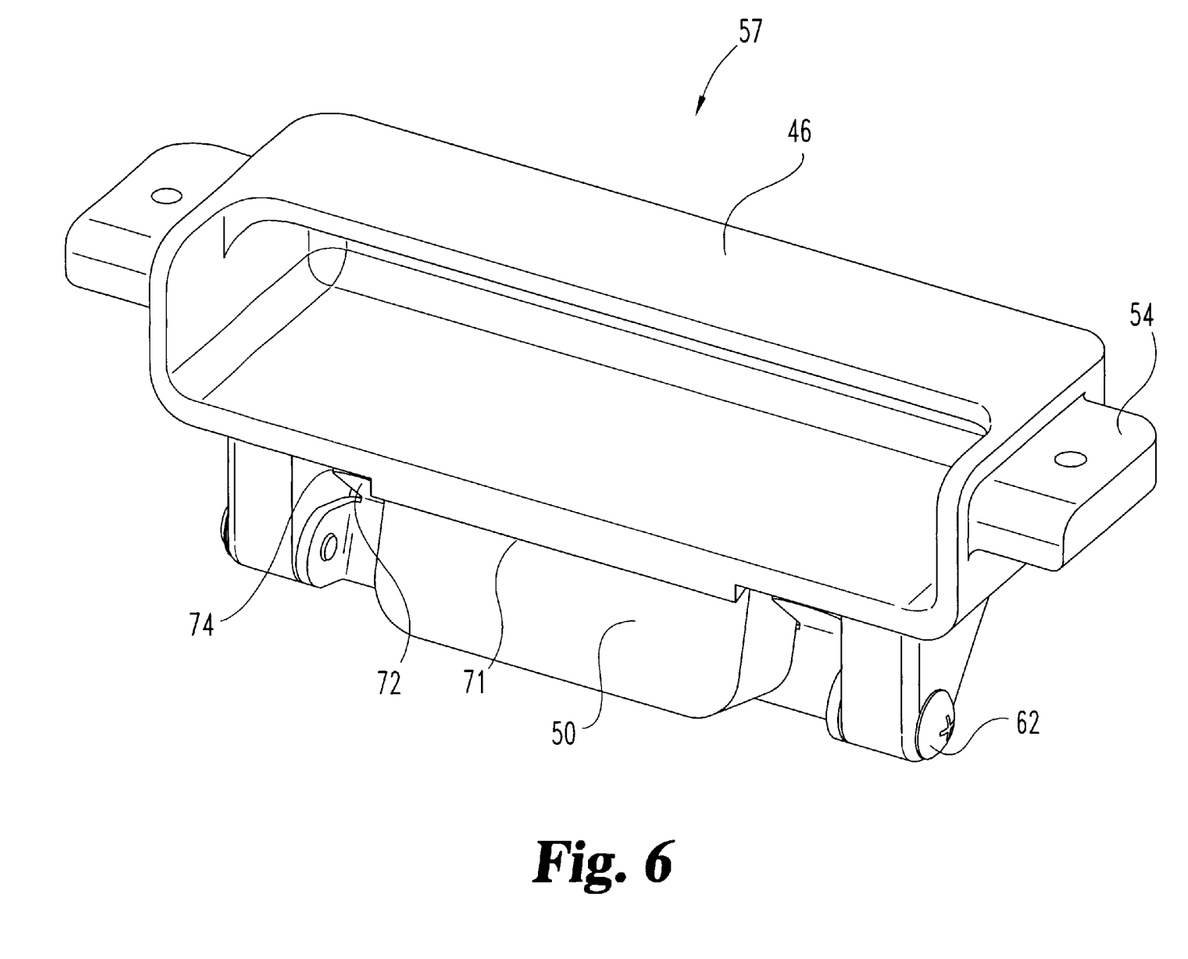

Latchplate 60 incorporates a pair of tabs 72 moveable with latchplate 60 and button 50. These moveable tabs 72 extend upward and outward at an angle as best seen in FIG. 5. Moveable tab 72 has an edge 74 which is proximate to the underside of stationary tab 52 when lid 22 is releaseably coupled to sides 24a and 24b. Thus, when container 20 is picked up by handle 46, edge 74 of moveable tab 72 engages the underside of tab 52 and does not permit lid 22 to uncouple from sides 24a and 24b. To release lid 22 from its coupling with sides 24a and 24b, button 50 is pushed in along upper surface 71 of button 50 (see FIG. 6). Button 50, latchplate 60, and moveable tabs 72 will thus rotate into the interior of container 20. As moveable tabs 72 pivot, edge 74 moves past edge 76 of stationary tab 52. Once edge 74 has moved clear of edge 76, lid 22 may be lifted vertically and uncoupled from sides 24a and 24b. As upper surface 71 of button 50 is Dushed inward toward the interior of container 20, semi-circular guide 75 of handle assembly 57 provides a guide for guided surface 77 of button 50 (see FIG. 8).

Although button 50 and moveable tabs 72 have been shown and described as moving in a pivotal manner, the present invention also contemplates a button and moveable tabs that move linearly within container 20 when pushed. This linear movement button and linear movement tabs would be guided along support rails coupled to supports extending from the handle. The means for releaseably coupling lid 22 to container 20 includes a stationary tab 52, a moveable tab 72. and a button 50 for moving moveable tab 72, the movement being rotational, linear, or a combination of the two.

Figure 7:
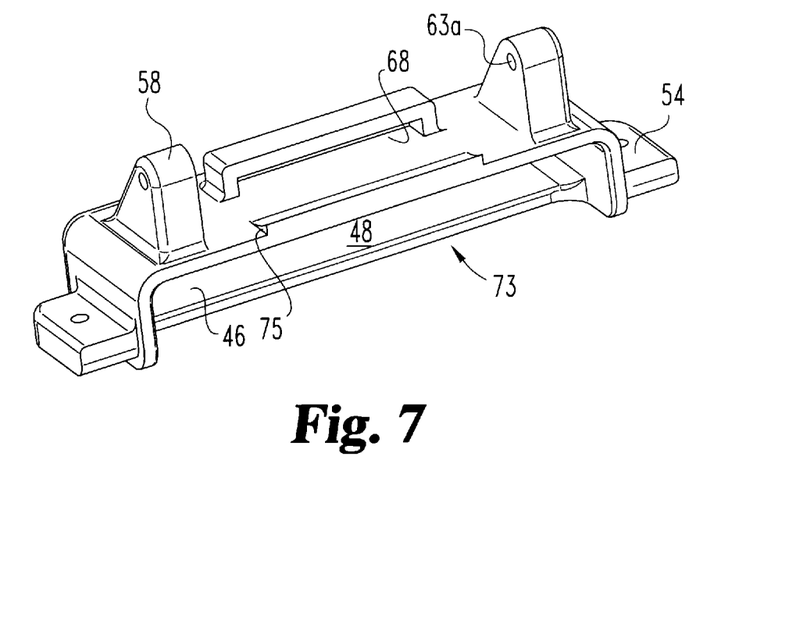
FIG. 7 is a perspective view of a handle molding comprising a portion of the present invention.
Figure 8:
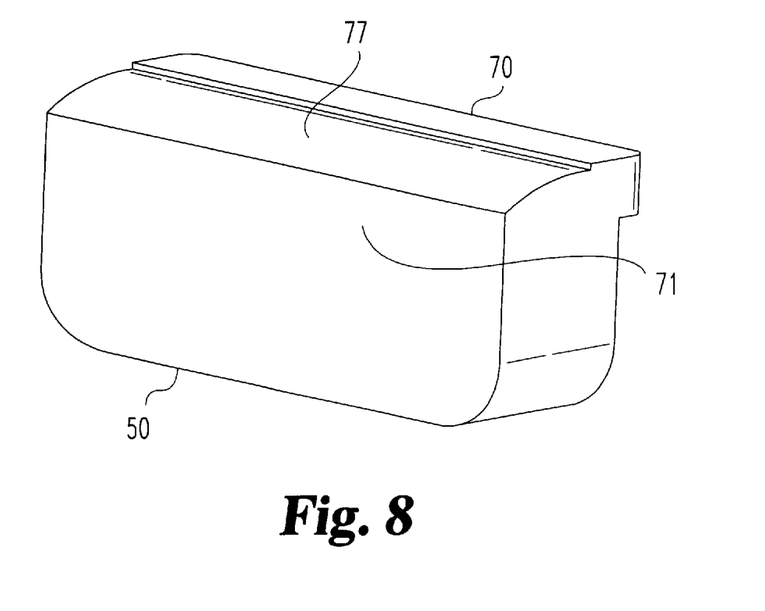
FIG. 8 is a perspective view of a button comprising a portion of the present invention.

A handle molding 73 comprising a portion of the present invention is shown in FIG. 7. Handle molding 73 shows a preferable combination of handle 46, ears 54, supports 58, spring retainer 68, and semi-circular guide 75, all molded within a single part. However, the present invention also contemplates those embodiments in which the aforementioned pieces may be separately fabricated and attached together as an assembly.

Figure 9:
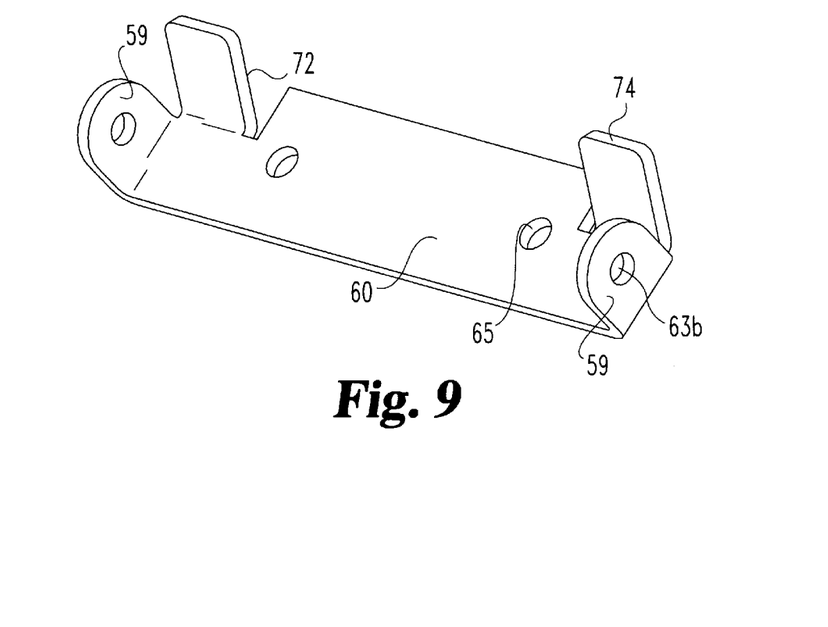
FIG. 9 is a perspective view of a latchplate comprising a portion of the present invention.

Latchplate 60 is shown apart from button 50 in FIG. 9. In a preferred embodiment, plate 60 is fabricated from a metal such as a corrosion resistant stainess steel. However, the present invention also contemplates those embodiments in which moveable gabs 74 are molded integrally onto button 50.

Figure 10:
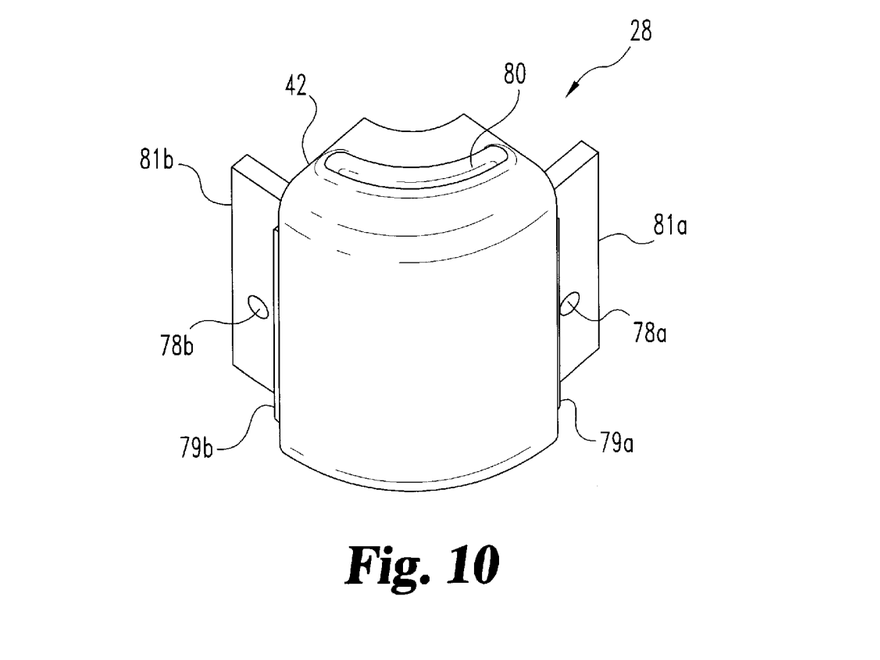
FIG. 10 is a perspective view of a corner piece comprising a portion of the present invention.

FIG. 10 is a top perspective view of a corner piece 28 comprising a portion of the present invention, and shown previously as corner pieces 28a, 28b, 28c, and 28d. Corner piece 28 has a generally smooth, rounded exterior surface and encompasses about 90 degrees of circular arc. Preferably projecting from either end 79a and 79b of corner piece 28 is an attachment ear 81a and 81b, respectively. A side 24a, 24b, 26a, or 26b may be attached to a corner piece 28 by placing the edge of the side in contact with surface 79a, and the interior surface of the side in contact with attachment 81a. A fastener fastens a side 26a, 26b, 24a, or 24b to corner piece 28 through fastener bole 78a. By removing the fastener from fastener hole 78a, corner pieces 28 are separable from container 20. For simplicity of manufacturing and assembly and reduction in cost, corner pieces 28a, 28b, 28c, and 28d, are preferably identical. The present invention also contemplates a corner piece in which the attachment ears are integrated into the separable sides, and the corner piece includes a pocket shaped to slidable accept the attachment ear.

Corner 28 includes a smooth, recessed first locating feature 80 on the top surface of corner 28. This first locating feature 80 is capable of being coupled to a second raised locating feature 82 on the bottom of corner piece 28 (refer to FIG. 3). Locating features 80 and 82 are useful for stacking of one container 20 on top of another container 20. Raised locating feature 82 can be coupled within recessed locating feature 80 and thus stabilize the position of the top container 20 relative to the position of the bottom container 20. It is preferable that locating features 80 and 82 be complementary in shape, such that the shape of feature 82 fits within the recessed shape of feature 80. It is also preferable that locating features 80 and 82 be incorporated on each corner piece 28. However, the present invention also contemplates those embodiments in which locating features 80 and 82 are present on only two of the corner pieces. Further, the present invention also contemplates a locating feature 82 that couples to locating feature 80, but is not necessarily complementary in shape thereto.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A container for sterilization of medical devices which comprises:

a plurality of separable sides;

a plurality of separable corner pieces, each of said plurality of separable sides being coupled to at least one of said separable corner pieces; and a separable bottom panel, said separable bottom panel being coupled to at least one of said separable sides or said separable corner pieces;

wherein each said separable side includes an upper surface, at least one said separable corner piece is between two said separable sides, and said one separable corner piece includes a first alignment feature spaced above the upper surface, and which further comprises a lid releaseably coupleable to at least one of said separable sides, said lid including a second alignment feature complementary to said first alignment feature, the first alignment feature and the second alignment feature being coupled together when said lid is coupled to the one said separable side.

2. The invention of claim 1 wherein there are four said separable corner pieces and four said separable sides.

3. The invention of claim 1 which further comprises a lid releaseably coupled to at least one of said sides.

4. The invention of claim 1 wherein the number of separable corner pieces is equal to the number of separable sides.

5. The invention of claim 1 wherein one of said separable sides includes a first stationary tab, and which further comprises a removeable lid, said lid including a button coupled to said lid and moveable relative to said lid, said button including a second moveable tab connected to said button, said first stationary tab and said second moveable tab being engageable to couple said lid to the one of said sides, and said button being moveable to uncouple said lid from said side.

6. The invention of claim 1 wherein the container has a generally smooth exterior surface, and which further comprises a removeable lid, said lid being coupled to at least one of said separable sides, said lid including a handle, said handle defining a pocket for carrying the container, said handle being substantially flush with the exterior surface.

7. An apparatus which comprises:

a container for sterilization of medical devices, said container having a generally smooth exterior surface, said container including a plurality of sides and a lid, said lid defining at least one hole for passage of sterilization fluids, said lid being coupled to at least one of said sides, said lid including a handle, said handle defining a pocket for carrying the container, said handle being substantially flush with the exterior surface, wherein said sides are separable from said container, and which further comprises a plurality of separable corner pieces, each said side being coupled to at least one of said separable corner pieces.

8. The invention of claim 7 which further comprises a first means for releaseably coupling said lid to one of said sides, said first coupling means being substantially flush with the exterior surface.

9. The invention of claim 8 which further comprises a second means for releaseably coupling said lid to one of said sides, said second coupling means being substantially flush with the exterior surface.

10. The invention of claim 7 wherein said lid includes a second handle, said second handle defining a pocket for carrying the container, said second handle being substantially flush with the exterior surface.

11. The invention of claim 7 wherein said sides are separable from said container, and which further comprises a plurality of separable corner pieces, each said side being coupled to at least one of said corner pieces.

12. A container for sterilization of medical devices which comprises:

four sides, each said side having an upper surface;

four corners, each said corner being adjacent two said sides, at least one said corner having a first alignment feature spaced above the upper surface of said adjacent sides; and a lid releaseably coupleable to at least one or said sides, said lid including a second alignment feature complementary to said first alignment feature;

wherein the first alignment feature and the second alignment feature are coupled together when said lid is coupled to the one said side.

13. The invention of claim 12 wherein said sides are separable from the container and said corners are separable from the container, each said side being coupled to at least one of said separable corners.

14. The invention of claim 12 wherein the container has an exterior surface and said lid includes a handle, said handle being substantially flush with the exterior surface.

15. An invention which comprises:

a container for sterilizing medical devices, said container including a plurality of separable sides and a removable lid, said container defining a plurality of holes for passage of sterilant therethrough, one of said sides including a first stationary tab, said removable lid including a button coupled to said removable lid and moveable relative to said removable lid, said button including a second moveable tab connected to said button, said first stationary tab and said second moveable tab being engageable to couple said removable lid to the one of said sides, and said button being moveable to uncouple said removable lid from said side, and a plurality of separable corners, each said separable side being coupled to at least one of said separable corners.

16. The invention of claims 15 wherein said button and said second tab are pivotable.

17. A container for sterilization of medical devices which comprises:

a plurality of separable sides;

a plurality of separable corner pieces, each of said plurality of separable sides being coupled to at least one of said separable corner pieces;

a separable bottom panel, said bottom panel being coupled to at least one of said separable sides or said separable corner pieces; and a lid releaseably coupleable to at least one of said separable sides, said lid defining a plurality of holes for passage of sterilant therethrough.

18. The invention of claim 17 wherein one of said separable sides includes a stationary tab, said lid including a button coupled to said lid and moveable relative to said lid, said button including a moveable tab connected to said button, said stationary tab and said moveable tab being engageable to couple said lid to the one of said separable sides, and said button being moveable to uncouple said lid from said separable side.

19. The invention of claim 17 wherein the container has a generally smooth exterior surface, said lid being coupled to at least one of said separable sides, said lid including a handle, said handle being substantially flush with the exterior surface of the container.

20. The invention of claim 17 wherein each of said separable sides has an upper surface, at least one of said separable corner pieces being adjacent two said separable sides, said one separable corner piece having a first alignment feature spaced above the upper surfaces of said adjacent separable sides, said lid including a second alignment feature complementary to said first alignment feature, wherein the first alignment feature and the second alignment feature are coupled together when said lid is coupled to the one said separable side.

21. The invention of claim 17 wherein there are four said separable corner pieces and four said separable sides.

22. The invention of claim 21 wherein the container has a generally smooth exterior surface, said lid being coupled to at least one of said separable sides, said lid including a handle, said handle being substantially flush with the exterior surface of the container.

23. The invention of claim 22 wherein each of said separable sides has an upper surface, at least one of said separable corner pieces being adjacent two said separable sides, said one separable corner piece having a first alignment feature spaced above the upper surfaces of said adjacent separable ides, said lid including a second alignment feature complementary to said first alignment feature, wherein the first alignment feature and the second alignment feature are coupled together when said lid is coupled to the one said separable side.

* * * * *